(12) United States Patent
Penque, Jr. et al.

(10) Patent No.: US 7,370,374 B2
(45) Date of Patent: May 13, 2008

(54) VENTILATED SAFETY GOGGLES

(75) Inventors: Frank P. Penque, Jr., North Tonawanda, NY (US); Wayne P. Phillips, Hudson, WI (US); Alan W. Reichow, Beaverton, OR (US); Karl Citek, Hillsboro, OR (US)

(73) Assignee: Jackson Products, Inc., Fenton, MO (US)

( * ) Notice: Subject to any disclaimer, the term of this patent is extended or adjusted under 35 U.S.C. 154(b) by 0 days.

(21) Appl. No.: 11/347,064

(22) Filed: Feb. 2, 2006

(65) Prior Publication Data

US 2006/0156457 A1 Jul. 20, 2006

Related U.S. Application Data

(63) Continuation of application No. 10/328,303, filed on Dec. 20, 2002, now Pat. No. 7,073,208.

(51) Int. Cl.
*A61F 9/02* (2006.01)
(52) U.S. Cl. .......................................................... 2/431
(58) Field of Classification Search ............ 2/435–437, 2/428, 431, 430
See application file for complete search history.

(56) References Cited

U.S. PATENT DOCUMENTS

| 1,296,707 | A |   | 3/1919  | Shindel |   |
|-----------|---|---|---------|---------|---|
| 1,322,834 | A |   | 11/1919 | Shindel |   |
| 1,582,785 | A |   | 4/1926  | Ratti   |   |
| 1,670,638 | A |   | 5/1928  | Shindel |   |
| 1,900,955 | A |   | 3/1933  | Shindel |   |
| 2,355,015 | A |   | 8/1944  | Splaine et al. | |
| 2,799,862 | A |   | 7/1957  | Rowe    |   |
| 2,877,463 | A |   | 3/1959  | Watkins |   |
| 3,031,675 | A |   | 5/1962  | Dubach  |   |
| 3,638,240 | A |   | 2/1972  | Militello | |
| 3,691,565 | A |   | 9/1972  | Galonek |   |
| 3,944,345 | A |   | 3/1976  | Decorato | |
| 4,264,988 | A | * | 5/1981  | Specht ........................... | 2/431 |
| 4,945,577 | A | * | 8/1990  | Hewitt et al. .................. | 2/437 |

(Continued)

FOREIGN PATENT DOCUMENTS

FR 2823317 A 10/2002

(Continued)

*Primary Examiner*—Katherine Moran
(74) *Attorney, Agent, or Firm*—Dunlap, Codding & Rogers, P.C.

(57) ABSTRACT

The invention is for safety goggles to protect eyes of a user of the safety goggles. The safety goggles include a lens and a frame with a bridge. A goggle chamber is formed between the lens and the face of the user. The safety goggles have a lower ventilation assembly that admits air one either side of the bridge. The safety goggles also includes an upper ventilation assembly at an upper portion of the frame. Air enters the goggle chamber through the lower ventilation assembly, heats near a nose of the user and exits the goggle chamber through the upper ventilation assembly. Each of the lower and upper ventilation assemblies cover a corresponding lower and upper air path in such a manner that allows air to pass through the corresponding air path while preventing solid projectiles and splashed liquid from having a direct line of trajectory to the eyes of the user.

2 Claims, 6 Drawing Sheets

U.S. PATENT DOCUMENTS

| | | | |
|---|---|---|---|
| 4,977,627 A * | 12/1990 | Metcalfe et al. | 2/437 |
| 5,027,443 A * | 7/1991 | Watkins | 2/437 |
| 5,519,896 A * | 5/1996 | Ford | 2/436 |
| 5,604,547 A | 2/1997 | Davis et al. | |
| 5,617,588 A | 4/1997 | Canavan et al. | |
| 5,802,622 A * | 9/1998 | Baharad et al. | 2/434 |
| 6,105,177 A | 8/2000 | Paulson et al. | |
| 6,149,268 A | 11/2000 | Hall et al. | |
| 7,058,991 B2 * | 6/2006 | Hartman et al. | 4/437 |

FOREIGN PATENT DOCUMENTS

| | | |
|---|---|---|
| WO | WO 03/050596 A1 | 6/2003 |
| WO | PCT/US 03/40821 | 5/2004 |

* cited by examiner

VENTILATED SAFETY GOGGLES

CROSS REFERENCE TO RELATED APPLICATIONS

The present application is a continuation of U.S. Ser. No. 10/328,303 filed Dec. 20, 2002, now U.S. Pat. No. 7,073,208, which is hereby expressly incorporated by reference herein in its entirety.

BACKGROUND OF THE INVENTION

1. Field of the Invention

The invention generally relates to eye protection devices and particularly to safety goggles that have ventilation to prevent fogging.

2. Description of the Related Art

People wear safety goggles and other protective eye wear in a variety of work environments to protect their eyes from solid projectiles, dust and splashed liquids. A problem that arises for certain types of safety goggles is that the safety goggles tend to form a fog on the inside of the lens and obstruct the vision of the wearer.

The typical solution to fogging has been to employ the use of anti-fog coatings on the lens, and augmenting the coating's performance by ventilating the ambient air that exists in the goggle chamber. This two component system minimizes the possibility of fog forming on the lens. Ambient air ventilation helps to prevent fogging by preventing heat build up in a goggle chamber formed between the safety goggles and the body of the wearer. However, when the safety goggles are provided with air ventilation, one must ensure that the ventilation mechanism does not provide a path for projectiles, hazardous liquids or dust particles to enter a goggle chamber between the eye and the safety goggles.

One problem encountered with safety goggles of the existing art is that these safety goggles do not provide sufficient air circulation to complement the lens coating and keep the safety goggles free of fogging and reducing heat accumulation. Air currents through the goggle chamber should cause the water vapor to be removed from the goggle chamber, thereby lowering the relative humidity. Previous designs for safety goggles have also not recognized that the human face has variations in temperature and have not properly accounted for these variations in designing safety goggles.

It has been established that in a typical goggle design, heat tends to accumulate in the area surrounding the wearer's nose.

To this end, a need exists for safety goggles which are simple in design, protect the eyes of the user, and which are inexpensive to manufacture. It is to such safety goggles that the present invention is directed.

DETAILED DESCRIPTION

Figure 1:
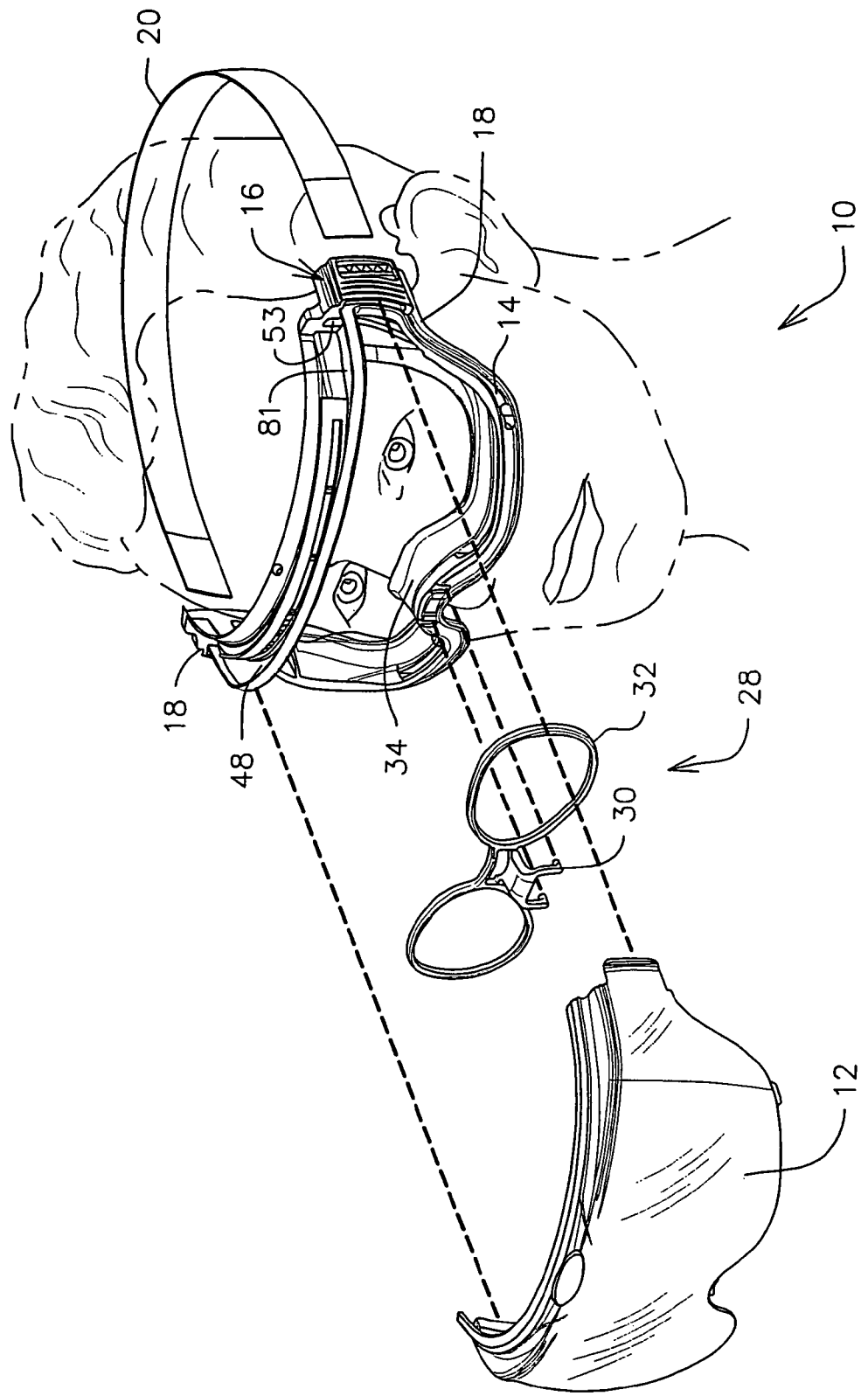
FIG. 1 is an exploded perspective view of the safety goggles constructed in accordance with a preferred embodiment of the invention.
Figure 2:
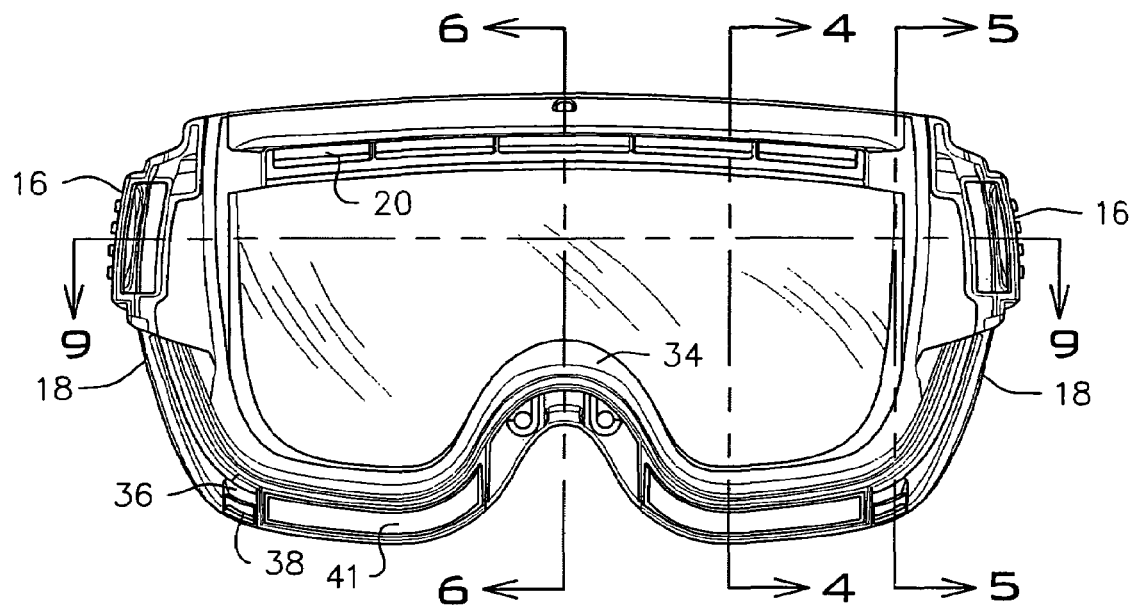
FIG. 2 is a rear elevation view of the safety goggles depicted in FIG. 1.

FIG. 1 shows a perspective view of a user wearing safety goggles 10 constructed in accordance with the present invention. The safety goggles 10 have a detachable unitary lens 12 attached to a frame 14. Although the lens 12 is shown to be unitary in FIG. 1, it is not important that the lens 12 be unitary and two lenses could also be used. Furthermore, the lens 12 could also be permanently fixed to the frame 14.

Figure 3:
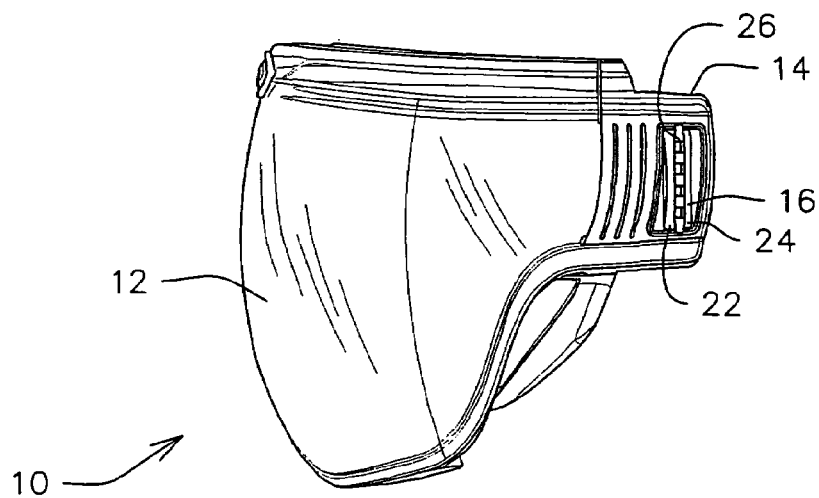
FIG. 3 is a side elevation view of the safety goggles depicted in FIG. 1.

As best seen in FIGS. 1 and 3, a pair of attachment assemblies 16 are located on opposite frame lateral portions 18 for attachment of a resilient flexible strap 20. The strap 20 fits over the head of a user and urges the frame 14 against the face of the user. For each attachment assembly 16, the strap 20 fits through two slots 22 and 24 separated by post 26 defined in the frame 14, as best seen in FIG. 3. Although the attachment assemblies 16 are shown to be two slots 22 and 24 defined on either side of a post 26, the resilient strap 13 could also be attached to the frame 14 by rigid fasteners, such as rivets, by an adhesive or by other suitable means.

Referring again only to FIG. 1, the safety goggles 10 may optionally include a secondary pair of glasses 28 attached to the frame 14 by a bracket 30. The secondary pair of glasses 28 includes a secondary frame 32 and two lenses (not shown). The lenses can be prescription lenses, sunglass lenses, or any other type of lenses. The secondary pair of glasses 28 enables a wearer of prescription glasses, for example, to use the secondary pair of glasses 28 as prescription glasses while wearing the safety goggles 10. The bracket 30 is attached to the frame 14 at a bridge 34 of the frame 14. The bridge 34 rests on the nose of the user.

FIGS. 2-8 show various views of the safety goggles 10, the frame 14 and the lens 12. The lens 12 has tabs 36 that fit into slots 38 to provide a "snap-fit" for the lens 12. In a preferred embodiment, the frame 14 is made as one piece from a plastic such as a rigid polymer. Examples of rigid polymers include polypropylene, polyethylene, or k-resin. In other preferred embodiments, the frame 14 is made of a pliable metal, or a mixture of plastic and metal. The lens 12 is typically made of a transparent, flexible plastic. The lens 12 has sufficient flexibility for the user to provide the snap-fit of the tabs 36 into the slots 38. Although the lens 12 is shown to attach to the frame 14 by way of tabs 36 and slots 38, the lens 12 may also attach to the frame 14 by other suitable means, such as by an adhesive or by removable fasteners such as screws, or clamp(s).

Figure 4:
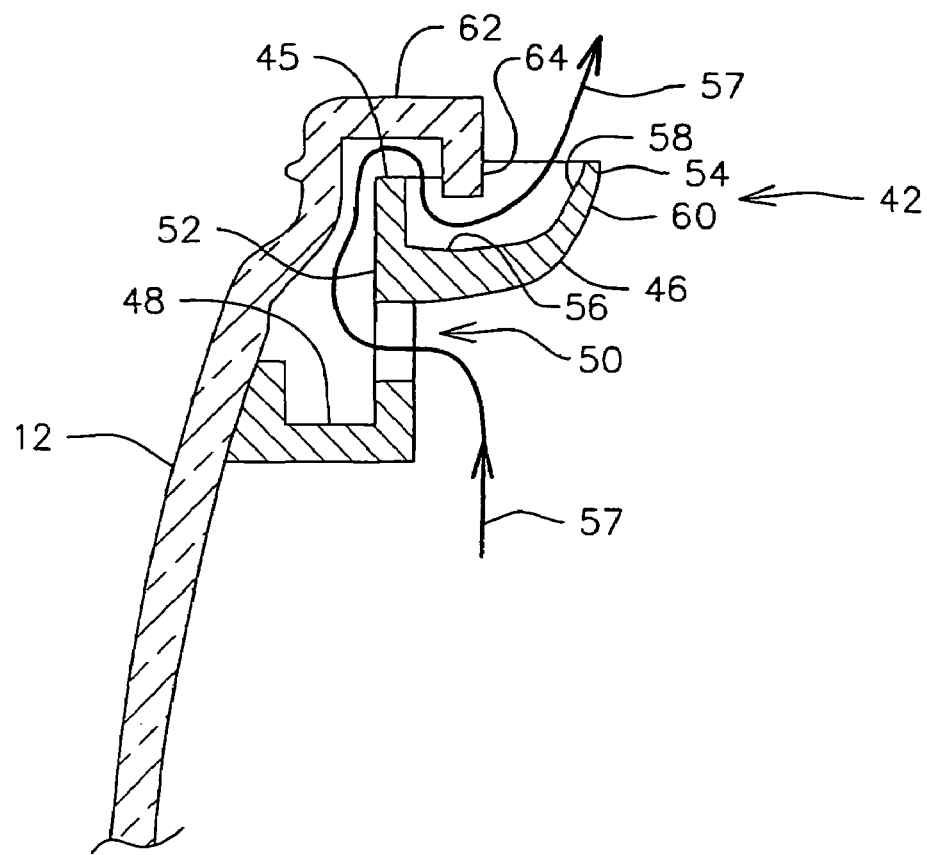
FIG. 4 is a cross sectional view of section 4-4 shown in FIG. 2.
Figure 4:
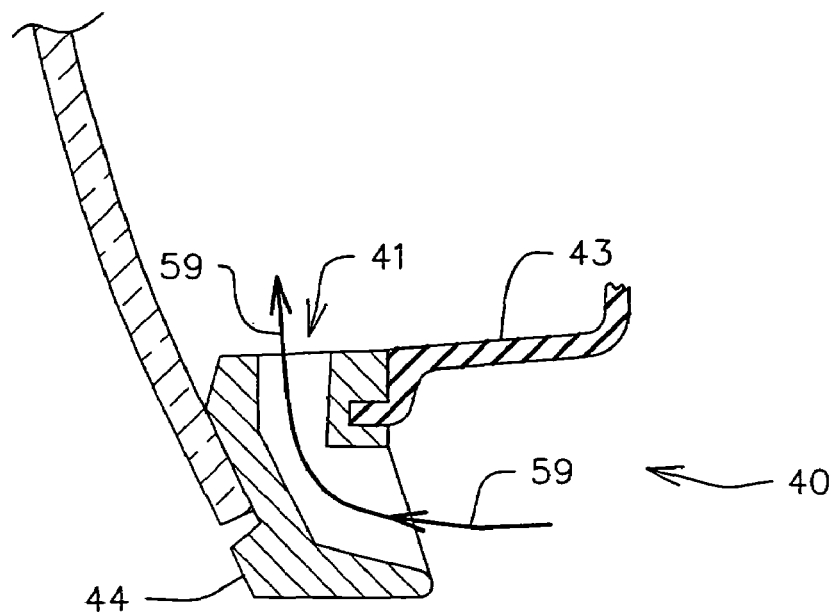

As best shown in FIG. 4, the safety goggles 10 have a lower ventilation assembly 40 and an upper ventilation assembly 42. In one preferred embodiment, the frame 14 is constructed of a flexible material to closely conform to the face of the user. A space located between the face of the user and the lens 12 is defined to be a goggle chamber.

The lower ventilation assembly 40 extends between the frame lateral portions 18. For the particular embodiment shown in FIGS. 1-6, the lower ventilation assembly 40 includes holes 41 formed in the frame 14. However, the holes 41 could also be formed in the lens 12 or between the lens 12 and the frame 14.

Again referring to FIG. 4, the lower ventilation assembly 40 is located near a frame lower portion 44 so that air entering the goggle chamber passes close to the cheekbones of the user and away from the face of the user as it passes through the lower ventilation assembly 40. Thus, the lower air path 59 is directed rearwardly from the frame 14 such that the cheek of the user shields any splashed liquid from directly entering the goggle chamber. The lower ventilation assembly 40 also includes a lower splash guard 43 to prevent splashed liquids from bouncing from the face of the user and entering the goggle chamber. The frame lower portion 44 cooperates with the lower splash guard 43 to define a lower air path 59 from the goggle chamber to the ambient air. In one preferred embodiment, the lower vent portion 44 utilizes a three-corner offset geometry to prevent the direct path of any particle from breaching the lower splash guard. Corner 41a, protrudes down and intersects the direct line that exists between corner 41c and 41b. This design conforms to the true definition of "indirect vent" as prescribed in ANSI Standard Z87.1-200X, section 8.9.2 "Indirect Ventilation." Line 41d denotes the end of the lower splash guard, and the area beyond this line is considered the internal goggle chamber.

The upper ventilation assembly 42 is located near a frame upper portion 45 and includes an upper splash guard 46 to keep splashed liquids from entering the goggle chamber through the upper ventilation assembly 42. The upper splash guard 46 forms a trough extending laterally for draining away any liquid which enters the trough. A channel 48 is positioned slightly below the upper splash guard 46 and slightly outward from the face of the user. The channel 48 is located to receive any splashed liquid that advances past the upper splash guard 46. The channel 48 and the upper splash guard 46 are sloped away from a center of the frame 14 so that any liquid that passes the upper splash guard 46 and collects in the channel 48 drains away from the center to the frame lateral portions 18. As can be seen in FIG. 1, the upper splash guard and the channel 48 drain to a basin 51 and through drain holes 53. The drain holes 53 are designed to be positioned just above and slightly forward from an ear of the user of the safety goggles 10.

One or more slits 50 are defined in a first wall 52 that extends upwardly from the channel 48. A lower portion of the first wall 52 defines a portion of the channel 48. The upper splash guard 46 is defined between the first wall 52 and a second wall 54. The second wall 54 extends upwardly from a horizontal portion 56 of the upper splash guard 46. The second wall 54 has an outside surface 58 and an inside surface 60. The inside surface 60 fits against the brow of the user in the embodiments shown in FIGS. 1-9.

A crown portion 62 of the lens 12 cooperates with the upper splash guard 46 and the channel 48 to restrict splashed liquid from entering the goggle chamber. Both the channel 48 and the lens crown portion 62 extend between the frame lateral portions 18. The lens crown portion 62 has a leg 64 extending for a portion of the distance between the frame lateral portions 18 in order to further restrict splashed liquid from entering the goggle chamber. The upper ventilation assembly 42 defines an upper air path 57 for air to exit the goggle chamber. The air path 57 conveys the "tortuous path" concept of the labyrinth vent design to minimize the possibility of liquids breaching the upper ventilation assembly 42.

It has been observed that the human face has an area of maximum heat concentration near the nose. This heat is transferred to air passing through the lower ventilation assembly 40 by convection. The heating of the ambient air entering the lower ventilation assembly 40 causes the air to rise and exit the goggle chamber through the upper ventilation assembly 42. Thus, an air flow path is established to draw ambient air into the goggle chamber through the lower ventilation assembly 40 and out of the goggle chamber through the upper ventilation assembly 42. Any moisture in the goggle chamber generated through skin of the user is transported out of the goggle chamber by the air flow.

The lower air path 59 and the upper air path 57 are tortuous or serpentine paths so that there is no direct line of trajectory into the goggle chamber from a liquid splash or a solid projectile generated outside the goggle chamber. Furthermore, because the air flowing through the lower ventilation assembly 40 or the upper ventilation assembly 42 must be turned by some portion of the lens 12 or frame 14, any dust particle entering the lower ventilation assembly 40 or the upper ventilation assembly 42 will collide with the upper or lower ventilation assembly 40 or 42 and surface tension will act to hold the dust particle to the upper or lower ventilation assembly 40 or 42.

Figure 5:
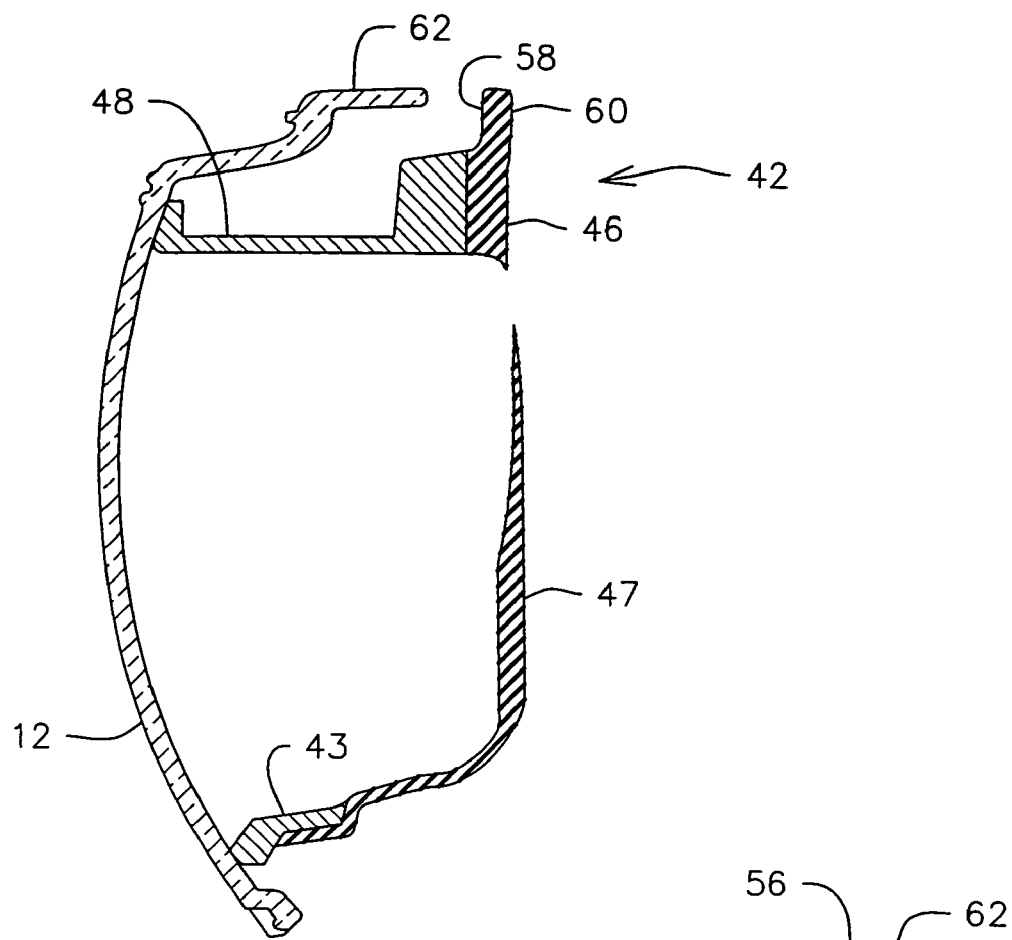
FIG. 5 is a cross sectional view of section 5-5 shown in FIG. 2.
Figure 6:
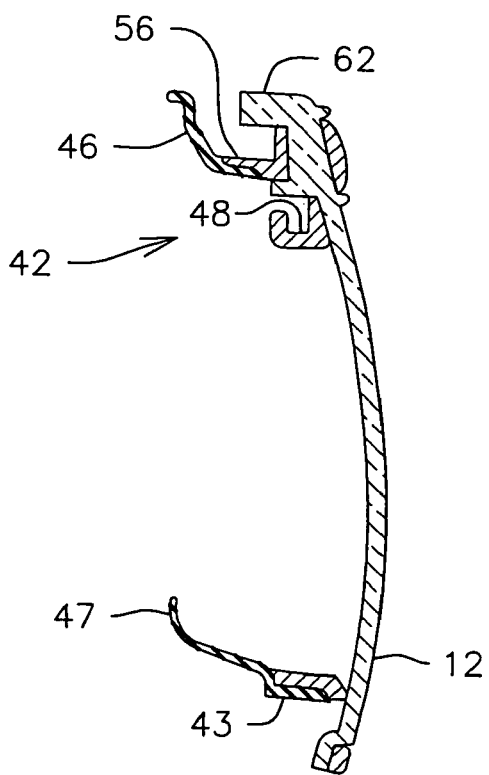
FIG. 6 is a cross sectional view of section 6-6 shown in FIG. 2.
Figure 7:
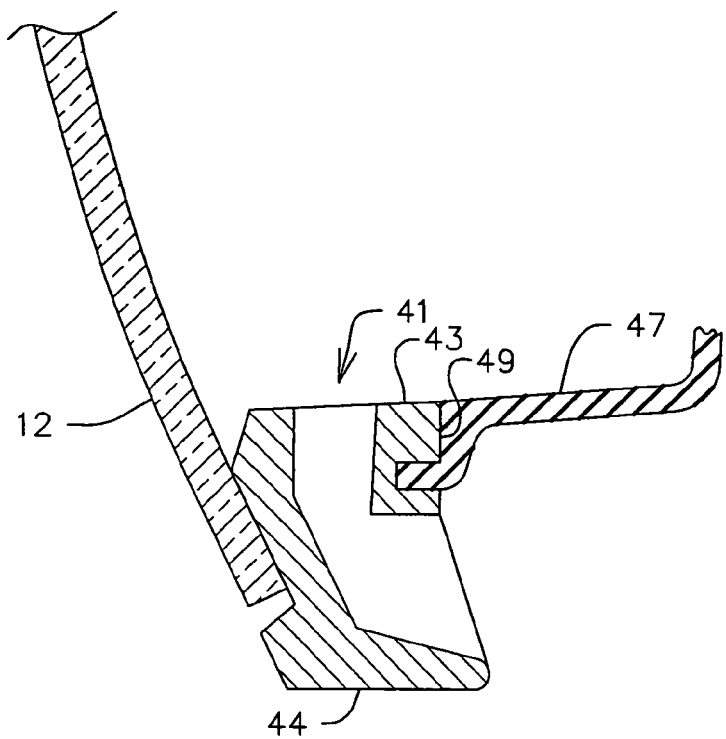
FIG. 7 is a cross sectional view of an alternate embodiment of the lower ventilation assembly shown in FIG. 4.

FIGS. 5-7 show embodiments of the safety goggles 10 that include a gasket 47 for providing a more compliant seal between the safety goggles 10 and the face of the user. The gasket 47 is made of a moldable, pliable compound, such as a thermoplastic elastomer (TPE), such as santoprene. The gasket 47 also provides more comfort for the user because the gasket is made of a softer material than the frame 14.

In a preferred embodiment, the gasket 47 is formed as part of a two-shot molding process. In the first shot, the plastic is put into a frame mold to form the frame 14 of the safety goggles 10. The plastic is allowed to cool and harden to provide a surface on the splash guard 43 against which the gasket 47 may be formed. In the second shot of the molding process, the moldable, pliable compound, such as TPE is put into a gasket mold to form the gasket 47. For the gasket mold, the splash guard 43 provides at least one of the molding surfaces of the mold. When the TPE, e.g., and plastic cool, the TPE and plastic form a chemical bond at a gasket/frame interface 49 shown in FIG. 7. The lens 12 is preferably formed in a lens mold separately from the frame 14 and assembled to the frame 14. The safety goggles 10 are completely assembled when the resilient strap 20 is attached to the safety goggles 10.

In yet another embodiment, the gasket 47 and the frame 14 are formed separately and an adhesive is applied at the gasket/frame interface 49. Next, the gasket 47 is brought into contacting engagement with the splash guard 43 and the adhesive is allowed to dry to attach the gasket 47 to the splash guard 43.

Figure 8:
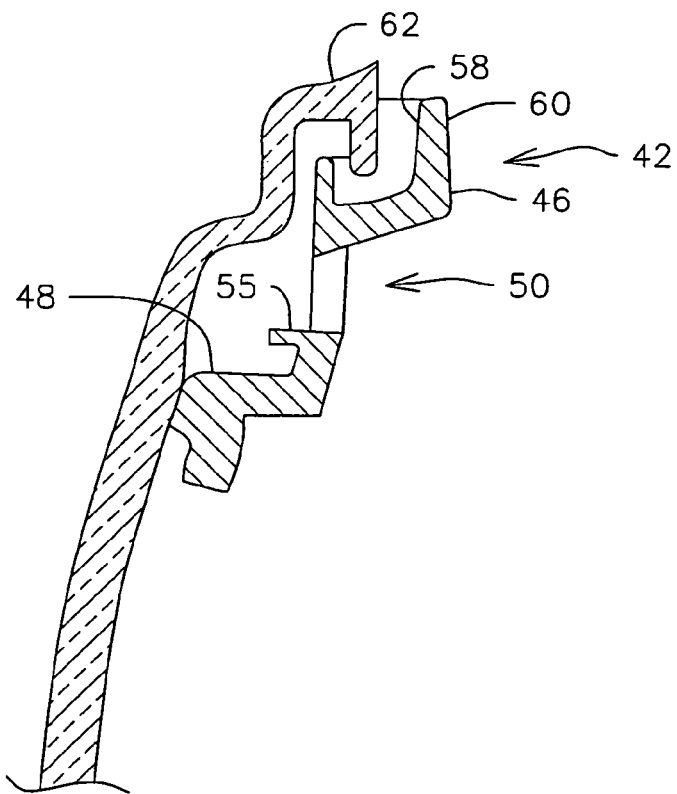
FIG. 8 is a cross sectional view of an alternate embodiment of the upper ventilation assembly shown in FIG. 4.

FIG. 8 shows another embodiment of the upper ventilation assembly 42 for the safety goggles 10. The embodiment shown in FIG. 8 differs from that shown in FIG. 4 in that the channel 48 has an upper horizontal surface 55 that prevents liquid in the channel 48 from being sloshed into the goggle chamber through the slits 50.

Figure 9:
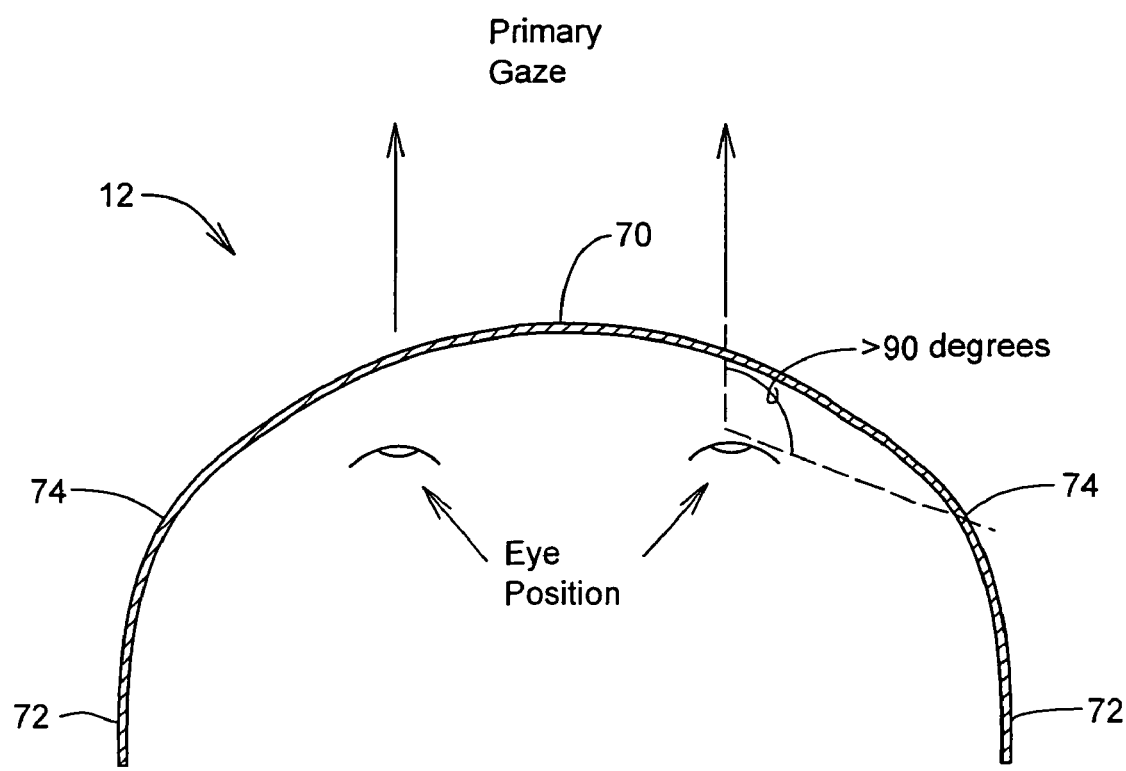
FIG. 9 is a cross sectional view of section 9-9 taken through the lens of the safety goggles shown in FIG. 3.

As shown in FIG. 9, the lens 12 is spherical, aspherical or cylindrical in shape along the viewing area 70 of the lens 12, and is typically flat or planar along lateral portions 72 of the lens 12. Although the lateral portions 72 are typically flat, it should be understood that other shapes of the lateral portions 72 can be used. The lens 12 changes thickness such that the thickest portion of the lens 12 is in the area near the bridge 34 and tapers so that the thinnest portion of the lens 12 is near transition zones 74 close to the lateral portions 72 of the lens 12. The transition zones 74 are the regions in the lateral portions 72 of the lens 12 where the curvature changes from the spherical, aspherical or cylindrical shape in the viewing area 70 to the lateral portions 72 in a continuous manner. In one preferred embodiment, for each of the transition zones 74, the radius of curvature of the lens 12 increases from the radius of the lens 12 in the viewing area 70 to infinity in the lateral portions 72. Other shapes of the transition zones 74 can be used.

In accordance with the present invention, the transition zones 74 are also positioned on the lens 12 beyond the peripheral vision in primary gaze and in an extreme periphery with maximum lateral gaze. The transition zones 74 are ninety degrees or more from the primary gaze (with the eyes looking straight ahead) in order to prevent the transition zones 74 from being in a field of view of the primary gaze. The transition zones 74 are positioned in the extreme periphery of vision with the maximum lateral gaze (the eyes looking as far to one side as is possible).

The following are the design specifications for one embodiment of the lens 12.

Component 1—spherical viewing area 70

| | |
|---|---|
| Front surface radius: | 3.850 in (97.79 mm) |
| Front surface curvature: | 5.41 Diopters |
| Back surface radius: | 3.824 in (97.13 mm) |
| Center (maximum) thickness: | 0.070 in (1.78 mm) |
| Edge (minimum) thickness: | 0.055 in (1.40 mm) |
| Total refractive power: | 0.00 Diopters |

Component 2—break or transition zone 74 (i.e., wrap area)

| | |
|---|---|
| Break start distance from center: | 2.900 in (73.66 mm) |
| Break end distance from center: | 3.375 in (85.73 mm) |
| Thickness: | 0.055 in (1.40 mm) |
| Front surface radius: | varies from 3.850 in (97.79 mm) to ∞ |
| Back surface radius: | varies from 3.824 in (97.13 mm) to ∞ |

Component 3—lateral portions 72

| | |
|---|---|
| Temple start distance from center: | 3.375 in (85.73 mm) |
| Angle with respect to frontal plane: | 93 deg |
| Thickness: | 0.055 in (1.40 mm) |
| Front and Back surface radii: | ∞ |

One skilled in the art will recognize many advantages of the safety goggles 10. For example, the lower and upper ventilation assemblies 40 and 42 are indirect in nature such that no direct line can breach the lower and upper ventilation assemblies 40 and 42 without changing direction. The upper ventilation assembly 40 is designed to provide a triple redundant system that requires encroaching liquid to breach two barriers, and overcome a strategically located drainage system before entering into the goggle chamber. The first barrier uses the geometry of the lens 12 and the frame 14 to block liquid from the goggle chamber. The second barrier is the channel 48, and the third barrier is the unique drainage system which is designed to channel any liquid that may breach the first barrier away from the goggle chamber. By sloping the channel 48 and the upper splash guard 46 toward the temple area, encroaching liquid is not allowed to accumulate to the point that it will breach the channel 48.

One further advantage of the embodiments shown in FIGS. 1-9 is that the safety goggles 10 can be formed using a molding process that does not require extensive assembly because the lower ventilation assembly 40 and the upper ventilation assembly 42 are formed once the lens 12 is attached to the frame 14. Designs for other systems have used several pieces to form the ventilation systems. The frame 14 of the safety goggles 10 of the present invention is molded in one shot and does not require that a worker manually strip the safety goggles 10 out of the frame mold. This in turn allows the safety goggles 10 to be formed with a relatively shorter molding cycle time.

From the above description, it is clear that the present invention is well adapted to carry out the objects and to attain the advantages mentioned herein as well as those inherent in the invention. While presently preferred embodiments of the invention have been described for purposes of this disclosure, it will be understood that numerous changes may be made which will readily suggest themselves to those skilled in the art and which are accomplished within the spirit of the invention disclosed and as defined in the appended claims.

What is claimed is:

1. Safety goggles worn by a user to protect the eyes of the user, the safety goggles comprising:
    a frame constructed as one piece, the frame having an upper frame portion, a lower frame portion, an interior side, and an exterior side; and
    a lens supported by the frame, the lens and the frame cooperating to form a goggle chamber between the lens and a face of the user;
    wherein the lower frame portion has a channel formed therethrough to allow air to flow between the goggle chamber and the exterior side of the frame, the channel configured to provide no direct linear path between the goggle chamber and the exterior side of the frame to prevent debris from entering the goggle chamber via the channel along a linear path,
    wherein the channel comprises a first end and a second end, the first end having an opening into the goggle chamber and the second end having an opening facing rearwardly toward the face of the user when the goggles are worn by the user, the face of the user cooperating with the opening of the second end to further prevent debris from entering the goggle chamber.

2. The goggles of claim 1 further comprising a lower splash guard supported by the frame, the lower splash guard extending away from the lower frame portion to contact the face of the user and prevent debris from entering into the goggle chamber.

\* \* \* \* \*